(12) United States Patent
Rodriguez

(10) Patent No.: US 9,619,614 B2
(45) Date of Patent: Apr. 11, 2017

(54) METHOD, APPARATUS, AND COMPUTER-READABLE MEDIUM FOR INTEGRATING AND SHARING PATIENT-RELATED INFORMATION VIA AN AUTHENTICATED APPLICATION PROGRAMMING INTERFACE

(71) Applicant: Roberto Rodriguez, Bryn Mawr, PA (US)

(72) Inventor: Roberto Rodriguez, Bryn Mawr, PA (US)

( * ) Notice: Subject to any disclaimer, the term of this patent is extended or adjusted under 35 U.S.C. 154(b) by 115 days.

(21) Appl. No.: 14/612,518

(22) Filed: Feb. 3, 2015

(65) Prior Publication Data

US 2015/0220686 A1    Aug. 6, 2015

Related U.S. Application Data

(60) Provisional application No. 61/935,221, filed on Feb. 3, 2014.

(51) Int. Cl.
| | |
|---|---|
| *H04L 9/32* | (2006.01) |
| *G06F 19/00* | (2011.01) |
| *H04L 29/06* | (2006.01) |

(52) U.S. Cl.
CPC ............ *G06F 19/322* (2013.01); *H04L 63/08* (2013.01); *G06F 19/328* (2013.01); *G06F 19/363* (2013.01)

(58) Field of Classification Search
CPC ..... H04L 63/08; H04L 63/10; G06F 21/6227; G06F 21/30; G06F 21/31; G06Q 50/22; G06Q 50/24

USPC ...... 726/2-4, 26-30; 713/168, 193; 705/2, 3
See application file for complete search history.

(56) References Cited

U.S. PATENT DOCUMENTS

| | | | |
|---|---|---|---|
| 7,143,284 B2 * | 11/2006 | Wheeler ................. | G06F 21/32 705/76 |
| 8,000,977 B2 * | 8/2011 | Achan .................. | G06Q 10/103 705/2 |
| 8,027,846 B2 | 9/2011 | Schoenberg et al. | |
| 8,112,817 B2 * | 2/2012 | Chiruvolu ............... | G06F 21/31 726/26 |
| 8,533,746 B2 * | 9/2013 | Nolan ................... | G06F 19/322 705/2 |
| 8,805,702 B1 * | 8/2014 | Daniel .................. | G06F 19/323 235/380 |

(Continued)

*Primary Examiner* — Hosuk Song
(74) *Attorney, Agent, or Firm* — Reed Smith LLP; Robert R. Riddle; Amardeep S. Grewal

(57) ABSTRACT

An apparatus, computer-readable medium, and computer-implemented method for integrating and sharing patient-related information among members of a medical team in real-time via an authenticated Application Programming Interface (API), includes receiving preliminary patient data corresponding to the patient from a first member of a medical team comprising a plurality of members, the preliminary patient data being received via the authenticated API, generating a patient profile for the patient, the patient profile being accessible to each member of the medical team via the authenticated API, receiving input relating to the patient from a second member of the medical team, the input being received via the authenticated API, and updating the patient profile based at least in part on the received input, with each of the plurality of members of the medical team being able to access the updated patient profile via the authenticated API.

27 Claims, 22 Drawing Sheets

(56) References Cited

U.S. PATENT DOCUMENTS

| | | | |
|---|---|---|---|
| 8,850,533 B2 * | 9/2014 | McLaren | G06F 19/322 705/2 |
| 2004/0111293 A1 | 6/2004 | Firanek et al. | |
| 2008/0208618 A1 | 8/2008 | Schoenberg et al. | |
| 2013/0152005 A1 | 6/2013 | McLaren et al. | |

* cited by examiner

METHOD, APPARATUS, AND COMPUTER-READABLE MEDIUM FOR INTEGRATING AND SHARING PATIENT-RELATED INFORMATION VIA AN AUTHENTICATED APPLICATION PROGRAMMING INTERFACE

RELATED APPLICATION DATA

This application claims priority to U.S. Provisional Application No. 61/935,221, filed Feb. 3, 2014, the disclosure of which is hereby incorporated by reference in its entirety.

BACKGROUND

Patients frequently require treatment by multiple medical professionals working as a team. For example, a patient may require treatment or a surgery that requires coordination between a cardiologist, multiple surgeons, and multiple nurse practitioners. Additionally, for many intensive surgeries, such as Transcatheter Aortic Valve Replacement (TAVR), there are stringent guidelines and requirements that must be met before the operation can be performed.

TAVR is a procedure for select patients with severe symptomatic aortic stenosis (narrowing of the aortic valve opening) who are not candidates for traditional open chest surgery or are high-risk operable candidates. The Centers for Medicare & Medicaid Services (CMS) require extensive documentation for the patient to qualify for the surgery. Additionally a cardiovascular team is required to perform the implant and must document all patient implants. Furthermore, expensive data acquisition post implantation is required to be submitted to the Society of Thoracic Surgeons (STS) and the American College of Cardiology (ACC) Trans-catheter Valve Therapy (TVT) registry.

As a result, communication and coordination between members of a medical team regarding a particular patient is of paramount importance. Additionally, documentation of all information relating to the patient and communications between members of the medical team treating the patient is necessary to comply with requirements.

Current patient tracking systems focus only on patient records which are network based and which store only the medical history for the patient. There is currently no way to track the progress of a patient through a screening and referral process which involves multiple member medical teams. Additionally, there is currently no way to document, share, and communicate information regarding patient treatment in real-time among members of a medical team.

BRIEF DESCRIPTION OF THE DRAWINGS

FIGS. 9A-9I illustrate interfaces for accessing and editing patient evaluation forms according to an exemplary embodiment.

DETAILED DESCRIPTION

While methods, apparatuses, and computer-readable media are described herein by way of examples and embodiments, those skilled in the art recognize that methods, apparatuses, and computer-readable media for tracking a patient are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to.

Applicants have discovered a way of tracking, storing, communicating, and documenting data pertaining to a patient among members of a medical team. The present system allows a medical team to stay updated on the progress of a patient's treatment, facilitates data acquisition pertaining to the patient and the patient's treatment, enables coordination among members of a multidisciplinary medical team, and maximizes billing.

Figure 1A:
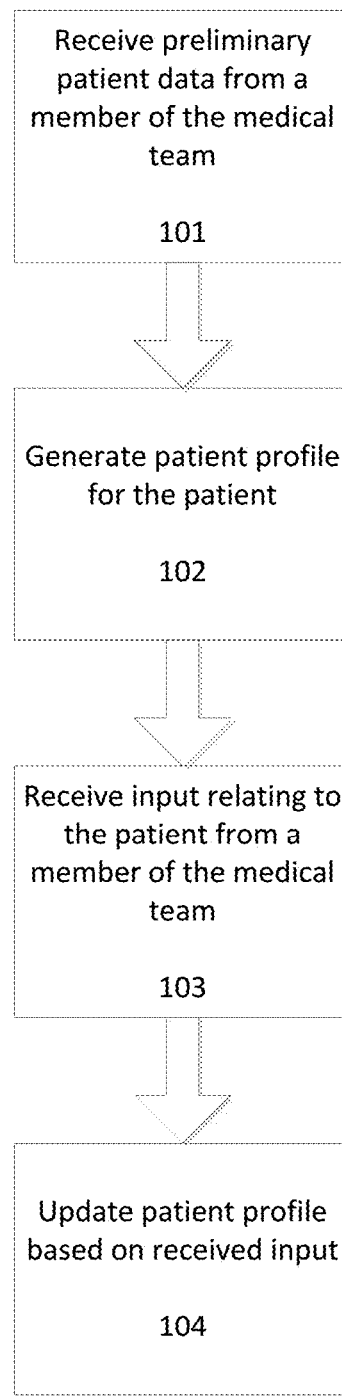
FIG. 1A illustrates a flowchart for tracking a patient according to an exemplary embodiment.

FIG. 1 is flowchart showing a method of tracking a patient according to an exemplary embodiment. At step 101 preliminary patient data corresponding to the patient is received from a member of a medical team. The medical team can include multiple members in different disciplines and roles. For example, the medical team can include cardiologists, surgeons, nurse practitioners, administrators, etc.

The preliminary patient data can be received via an authenticated Application Programming Interface (API). For example, the member of the medical team can enter the preliminary patient data into the authenticated API using the input of their mobile device and it can then be passed through the authenticated API to the system. The authenticated API can be a password-protected application running on mobile device, smart phone, or tablet. Alternatively, the authenticated API can be an application running on a mobile device which is registered to a member of the medical team, such that authentication is implicit. Of course, the authenticated API is not limited to mobile applications, and can be implemented as, for example, a website accessible through a browser or a software application running on a computer accessible to the medical team member. For example, a medical team member may navigate to a website and enter credentials, such as a user id and password, in order to access the authenticated API. In situations where security of the data and access is not necessary, the API may be implemented without authentication as well.

At step 102 a patient profile is generated for patient. The patient profile can be accessible to each member of the medical team via the authenticated API. Additionally, each member of the medical team can have differing privileges with respect to the patient profile. For example, some members of the medical team can have the ability to access and view the patient profile but not modify and information or add any information while other members of the medical team can have full reading and writing privileges. Additionally, the privileges of each member can differ according to different parts of the patient profile. For example, a surgeon team member can have the ability to edit portions of the patient profile relating to surgical recommendations but not portions of the patient profile relating to cardiogram results.

At step 103 input relating to the patient is received from a member of the medical team. The input can be received from either the same team member who provided the preliminary patient data or a different member of the medical team. Additionally, the input relating to the patient can be received via the authenticated API, such as through an interface on a mobile application. For example, a second member of the medical team can enter in the input into the authenticated API on their mobile device.

At step 104 the patient profile is updated based on the received input. This can include updating the profile with one or more results based on the input. This can also include annotating the profile with information corresponding to the input or completing some required information in the profile based on the input. For example, the input can be a note by one of the medical team members expressing an opinion or recommendation regarding a particular treatment option and the update can include the note in its entirety or an abbreviated version. The updated patient profile can then be accessed by each of the members of the medical team that have the requisite privileges via the authenticated API.

Figure 1B:
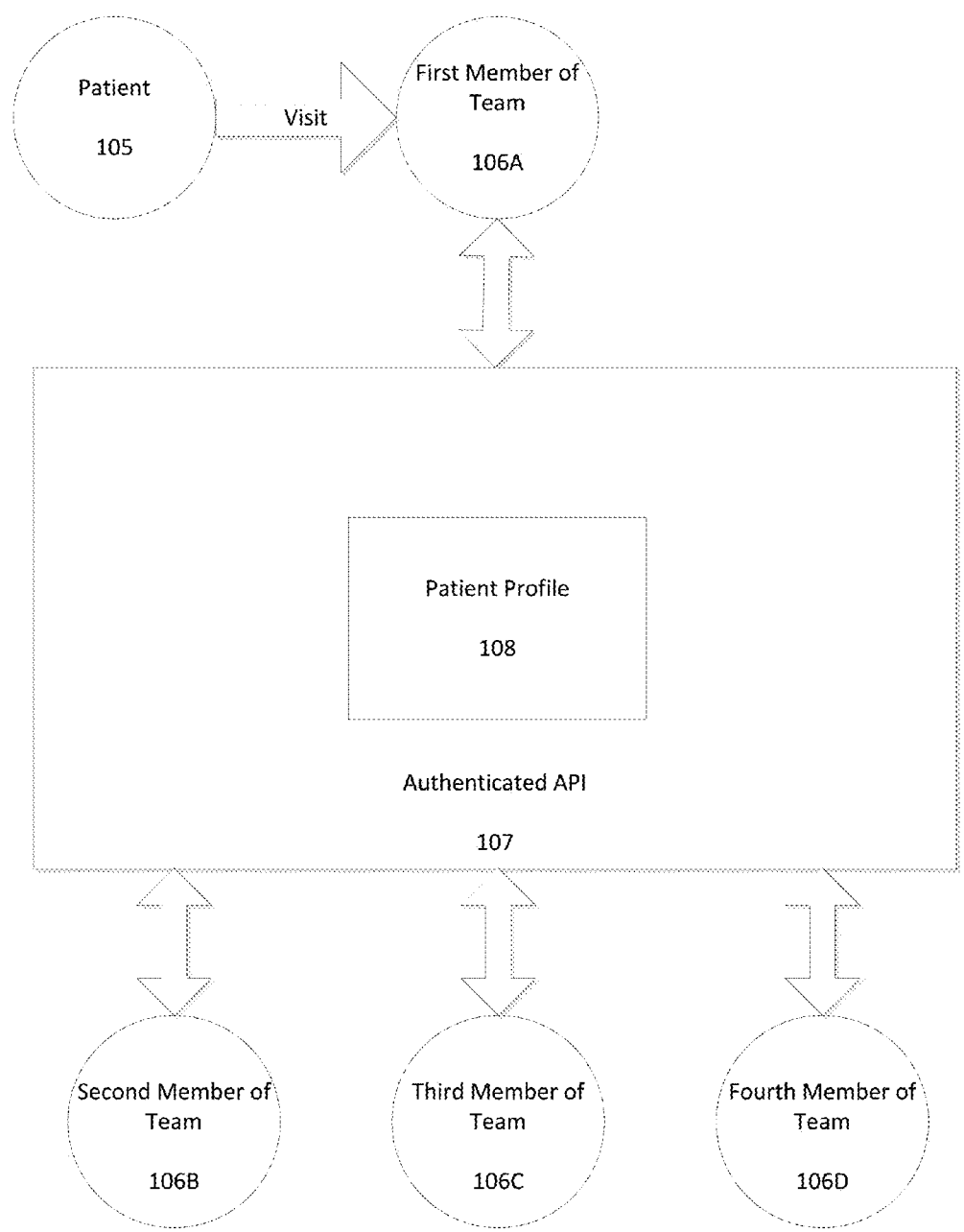
FIG. 1B illustrates a system for tracking a patient according to an exemplary embodiment.

Turning to FIG. 1B, a system and process flow diagram is shown with the members of a hypothetical four-member medical team. Of course, the diagram is for illustration only and the number of members of the medical team can be greater or fewer. Patient 105 can initially visit the first member of the team 106A. As a result of this visit, the first member 106A can acquire the preliminary patient data. The preliminary patient data can be provided directly by the patient 106 or it can be derived by the first member 106A based on tests conducted on the patient or measurements taken of the patient. Additionally the preliminary patient data can be provided to the first member 106A via electronic means, such as in an email or electronic record received by the first member 106A from a physician who previously treated the patient 105.

The preliminary patient data can include any information pertaining to the patient 105, such as demographic data (name, ages, sex, weight, height, medical record number, etc.), patient medical history, any previous or current test results, any previous or current measurements, and physician information for any physicians that have previously treated the patient or who referred the patient to the medical team member.

The preliminary patient data is received from the first member 106A via the authenticated API 107 and can be used to generate the patient profile 108. Alternatively, the patient profile 108 can be created beforehand by an administrator or a different member of the medical team and the preliminary patient data can added to the already existing patient profile 108.

As shown in FIG. 1B, the patient profile 108 is accessible to the second team member 106B, the third team member 106C, and the fourth team member 106D via the authenticated API. This means that any changes or updates to the patient profile 108 from one of the team members is made available to the other members of the medical team in real-time. This can be accomplished in multiple ways. For example, a common file corresponding to one or more patient profiles can be stored in the hospital network and made accessible only to team members. If the authenticated API is implemented as an application, the application can ask for a password and/or user id to verify that the user is a team member and has access to the common file. Once confirmed, the application can retrieve or access the common file and populate the relevant patient profile information. In this way, the authenticated API can be configured to detect and propagate any changes to the patient profile to the team members and their respective devices. Alternatively, the patient profile could be stored in an authenticated file sharing network and retrieved manually by team members having the necessary credentials. For example, the team member could open the application and see a prompt to load a file corresponding to a patient profile. The team member could then log in to a file-sharing service, such as Box™ or Dropbox™ to retrieve the file.

Any updates or changes to the patient profile 108 by one of the team members on a device of the team member can be propagated automatically via wireless or wired communication to the different devices of the other team members, such as by requiring the application to periodically synchronize the current version of the patient profile on the team members' devices with the version of the patient profile 108 stored in the common file. Additionally, the authenticated API 107 can be configured so that only one member of the medical team can make edits to the patient profile 108 at a time, limiting the other members to read-only privileges, such as by using a check-in/check-out system. Updates or changes made by any one of the team members can be stored locally on a local device, such as a tablet or computer, if the device does not have internet connectivity. Once connectivity is achieved, whether through the internet, a cellular phone plan, or a local area network, these changes can be propagated to the patient profile stored in the common file. Connectivity can also be achieved physically, without an internet or wireless connection, such as through a USB connection between a computer storing the common file and the team member's device.

Additionally, any updates to the patient profile or new information in the patient profile, such as information concerning diagnoses or operations, can automatically be transmitted to one or more registries, such as the TVT registry.

Figure 2A:
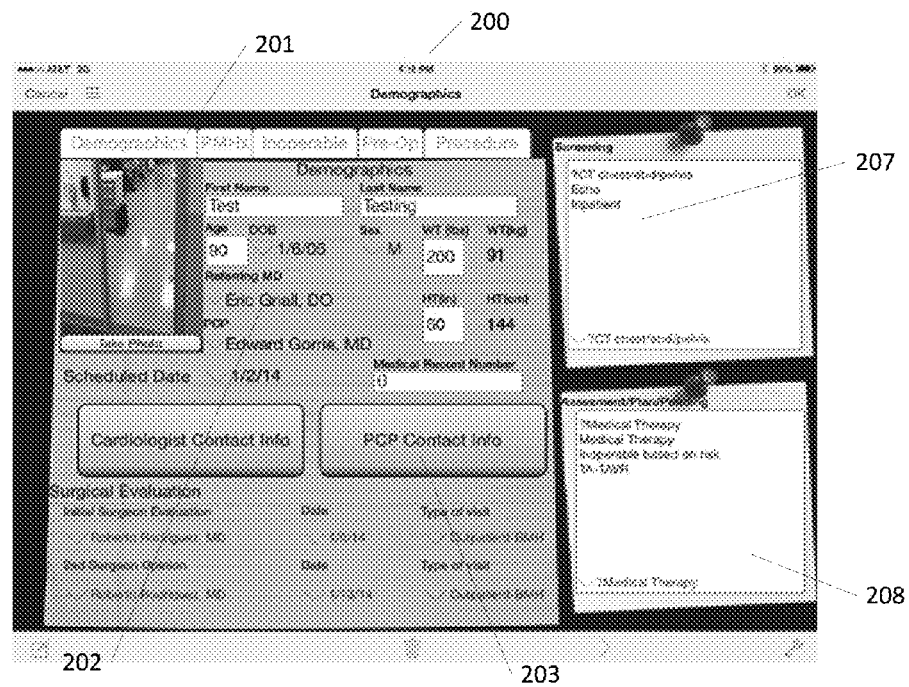
FIGS. 2A-2E illustrate interfaces for entering patient information and viewing patient history according to an exemplary embodiment.

Turning now to FIG. 2A, an interface 200 of the authenticated API is shown according to an exemplary embodiment. The interface 200 can include multiple windows or tabs 201. The tabs 201 in FIG. 2A include a "demographics" tab which is currently selected in the figure, a patient medical history (PMHx) tab, an "inoperable" tab which can be used to perform a variety of tests or complete a variety of evaluations pertaining to the patient, a "pre-op" tab which allows a team member to enter information necessary for an operation, and a "procedure" tab which can be used to document any procedures performed.

The specific examples shown and discussed in this application pertain to a TAVR patient. For example, the "inoperable" tab is used to perform a variety of tests or complete a variety of evaluations to determine if the patient is inoperable and thus a candidate for TAVR. Of course, the system disclosed herein can be customized to a variety of different practices, such as cardiac surgery, obstetrics, orthopedic surgery, oncology, general surgery, etc. For example, the authenticated API can be organized differently and/or include different tabs and interfaces than those presented in these specific examples. The systems and methods disclosed herein can also be customized to each hospital or practice where they are utilized. Additionally, the tabs in the exemplary interfaces presented herein are provided for illustration only, and the information and options available to users can be organized differently. For example, the interface of the authenticated API could have fewer tabs, including no tabs, in favor of a simplified or unified interface. Many variations are possible and these examples are not intended to be limiting.

As shown in FIG. 2A, the interface 200 for the demographics tab can contain all of the patient's demographics, including name, age, sex, weight, height, medical record number, etc. A user can also add or delete variables for different patient populations. The interface 200 can also include information regarding any physicians associated with the patient, such as a referring physician 202 or a primary care physician (PCP). Any of this information can be provided as part of the preliminary patient data or provided afterwards. The selection of a physician associated with the patient can be performed through the user interface, such as by using a drop down list or pop-up menu 202 as shown in FIG. 2A. If a team member using the interface 200 wishes to access contact information for a physician associated with the patient, they can request the information through the interface 200, such as by pressing a button 203 which links to the physician profile for the corresponding physician. Additionally, the interface 200 can present the results of any tests or screening conducted 207 or any assessments made 208 by any of the medical team members.

Interface 200 includes a "take photo" button which can be used to capture an image of the patient using a portable device of the user. For example, when the interface is shown on a portable device, such as a tablet, mobile phone, or laptop of the user, the user can select the "take photo" button and use the camera integrated with the portable device to take a photo. Additionally, the authenticated API of the present application can include functionality for capturing photos of documents, such as medical history forms, test results, and other patient information, which can then be converted and/or stored as documents in association with a digital medical file or data record of the patient.

Figure 2B:
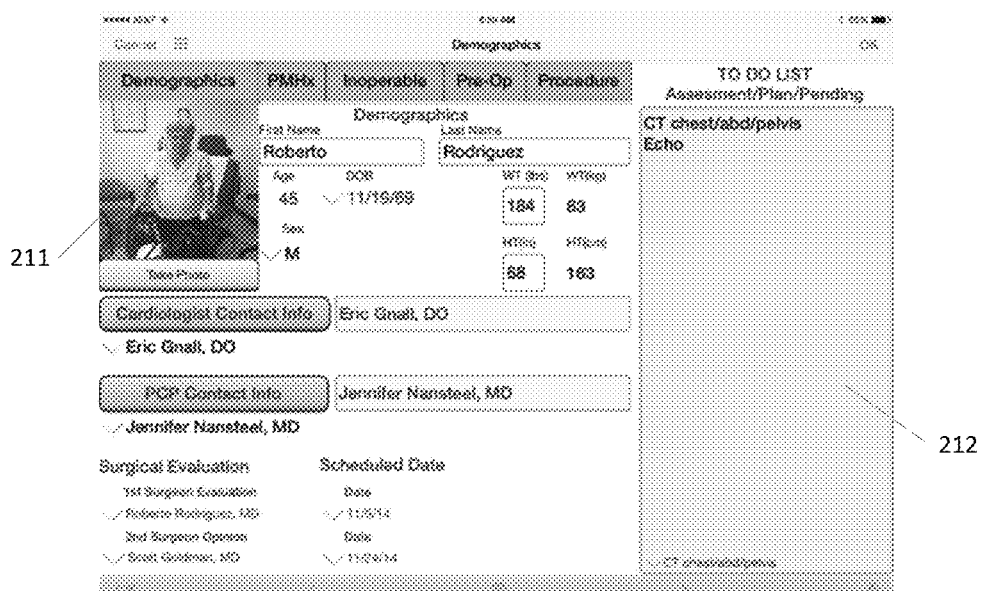

FIG. 2B illustrates another interface 210 that can correspond to the demographics tab. As shown in interface 210, the user has utilized the "take photo" button to capture a photo of the patient 211. This is similar to the "take photo" button shown as part of interface 200 in FIG. 2A. Additionally, as shown in FIG. 2B, a single window or user interface element 212 can be used to keep track of any upcoming assessments, tests, or screenings. As shown in FIG. 2B, a CT scan of the chest, abdomen, and pelvis is upcoming, along with an echocardiogram.

Figure 2C:
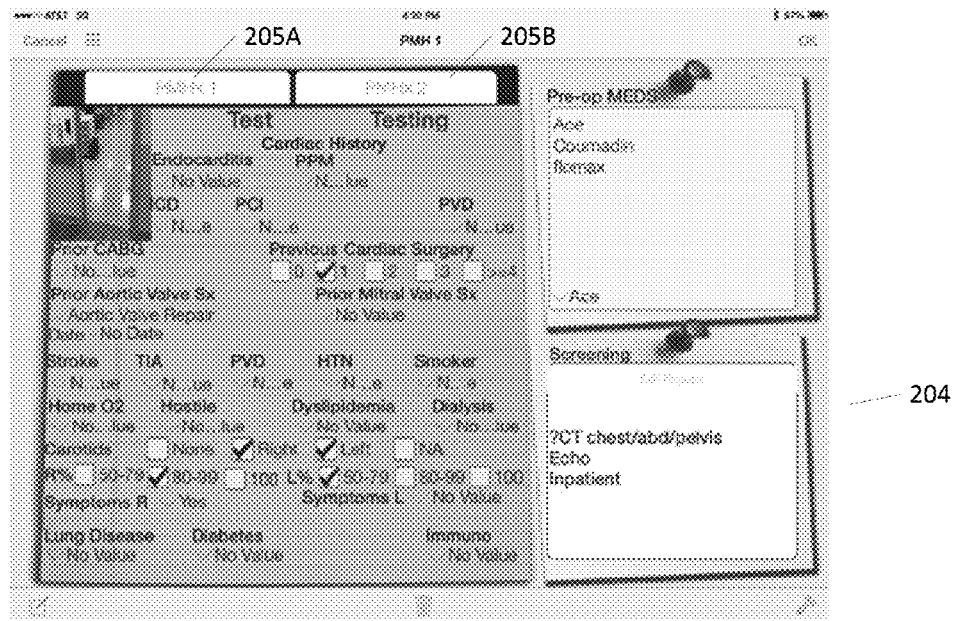
Figure 2D:
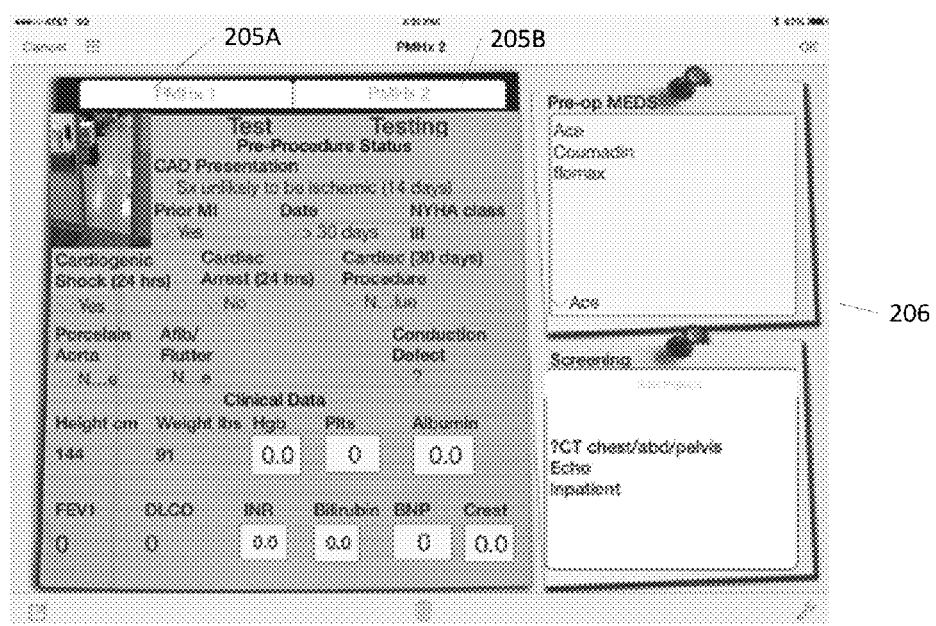
Figure 2E:
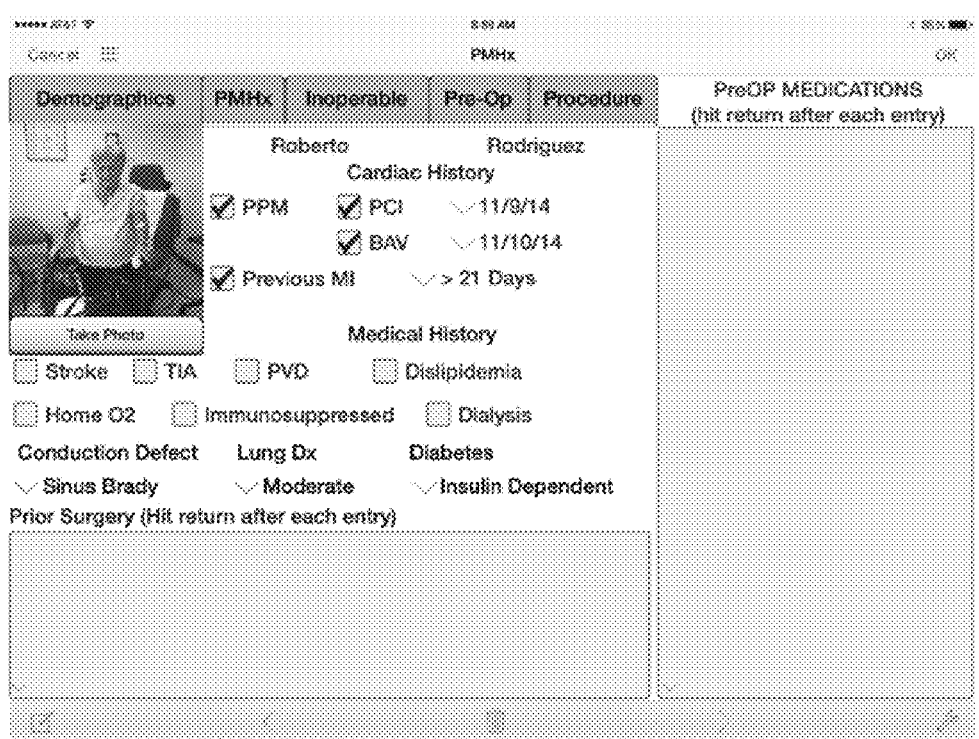

Turning to FIG. 2C, another interface 204 of the authenticated API is shown according to an exemplary embodiment. This interface 204 corresponds to a first sub-tab 205A of the PMHx tab and includes the patient cardiac history. In FIG. 2D, the interface 206 for the second sub-tab 205B is shown and includes the pre-procedure status of the patient. In the case of TAVR, the past medical history can include any history of diabetes, peripheral vascular disease, Chronic Obstructive Pulmonary Disease (COPD), myocardial infarcts, and coronary artery disease. FIG. 2E illustrates another interface 220 of the authenticated API which can also correspond to the PMHx tab. As shown in the interface 220 of FIG. 2E, all of the relevant patient medical history can be consolidated under a single tab, rather than two tabs, as shown in FIGS. 2C-2D.

Figure 3:
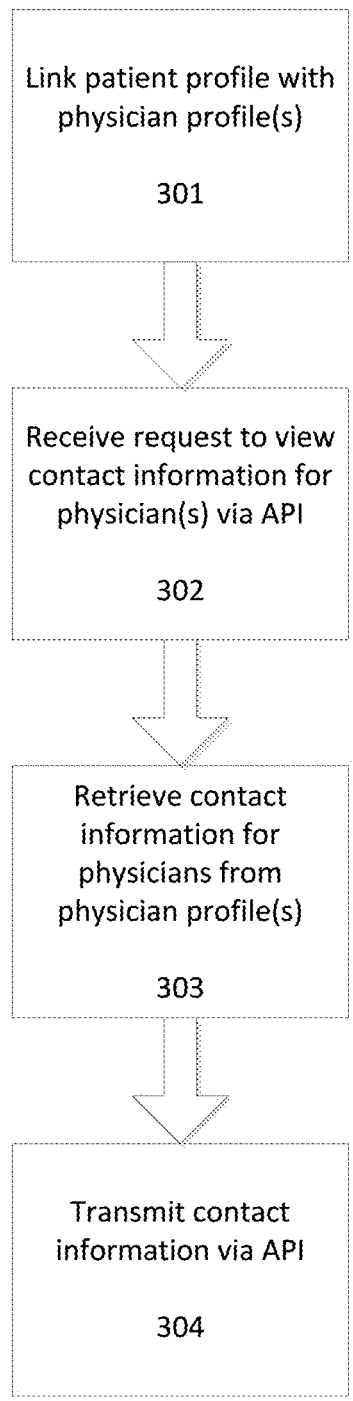
FIG. 3 illustrates a flowchart for retrieving contact information of a physician through an authenticated API according to an exemplary embodiment.

FIG. 3 is flowchart showing a method of retrieving contact information of a physician through the authenticated API according to an exemplary embodiment. At step 301 the patient profile is linked with a physician profile corresponding to a physician associated with the patient. For example, the patient profile can be linked with a physician profile corresponding to the patient's PCP or the patient's referring physician. The physician profile can be stored in a separate database accessible through the hospital network or through the internet. Alternatively, the physician profile can be stored in the common file under a different section. These examples are provided for illustration only and are not intended to be limiting. The linking can be performed by, for example, selecting the physician's name from a drop-down list, pop-up window, or other user interface element. Alternatively, the user may use the interface to select a file corresponding to the physician profile which is stored locally or remotely accessible.

At step 302 a request to view contact information for the physician associated with the patient is received via the authenticated API. This request can be received using a variety of means, such as an interface button, as shown in FIG. 2A, through a drop-down list or other interface element, or through an automated message (such as an e-mail) sent through the authenticated API.

Figure 4A:
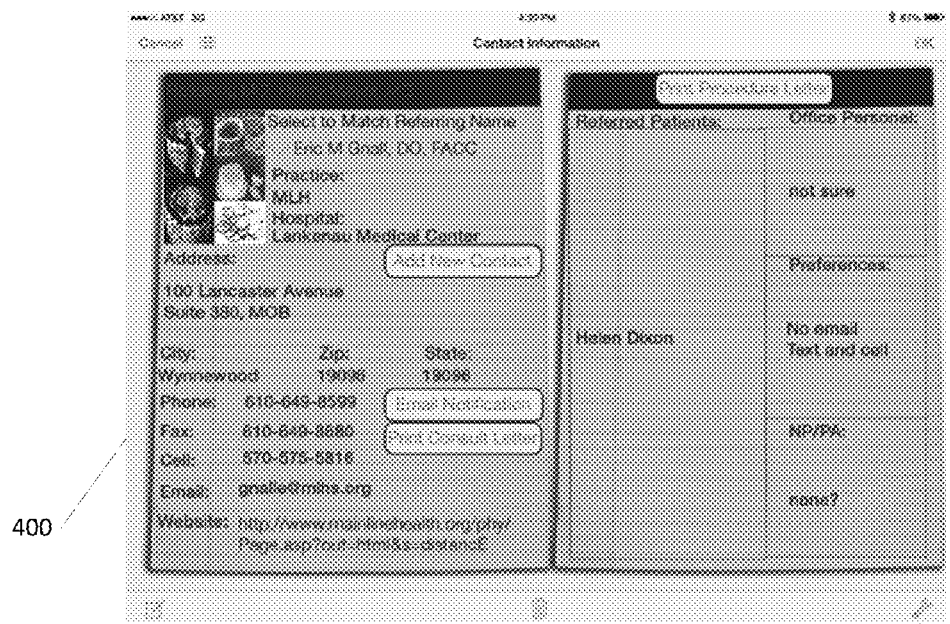
FIGS. 4A-4B illustrate interfaces for accessing physician contact information according to an exemplary embodiment.
Figure 4B:
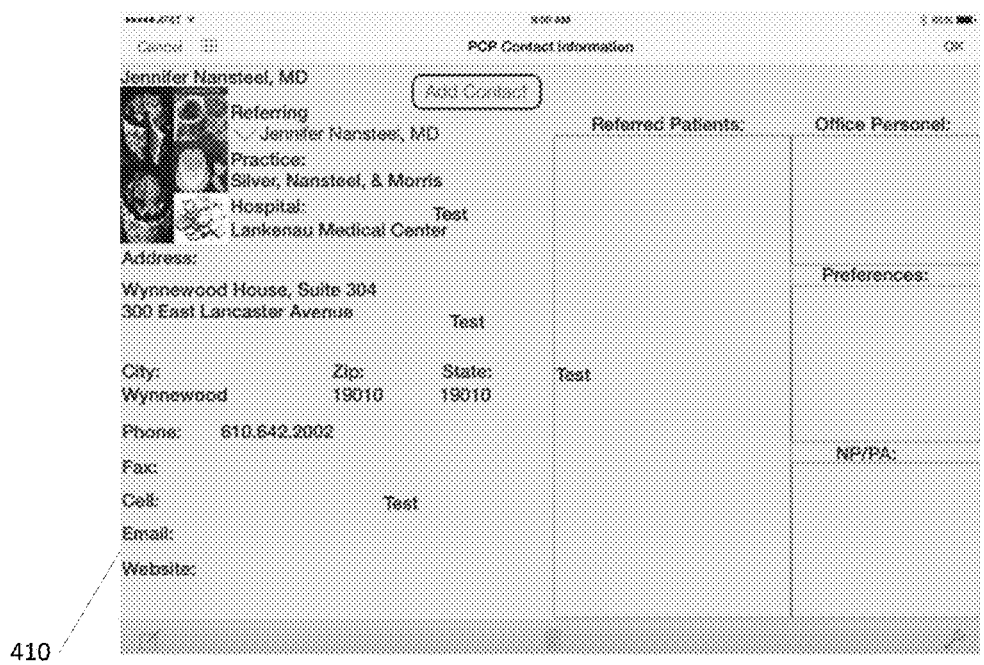

At step 303 the contact information for the requested physician is retrieved from the physician profile and at step 304 the contact information is transmitted via the authenticated API. For example, FIG. 4A illustrates an interface 400 of the authenticated API showing the contact information for a patient's referring physician and FIG. 4B illustrates an interface 410 of the authenticated API showing the contact information for a patient's primary care provider. Of course, the contact information can be delivered in other ways. For example, the contact information can be sent via email or SMS to an account or device associated with the requesting medical team member.

Figure 5A:
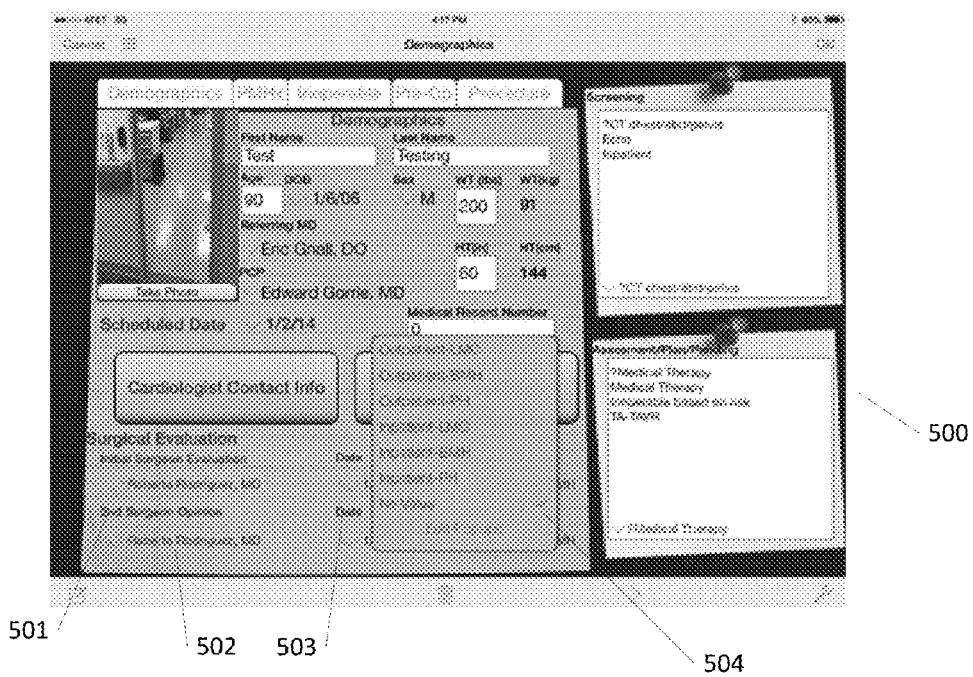
FIGS. 5A-5B illustrate additional interfaces of the authenticated API according to an exemplary embodiment.

Turning to FIG. 5A, another interface 500 of the authenticated API is shown according to an exemplary embodiment. The interface 500 shows a pop-up window 504 that appears when the user selects one of the adjustable options on the interface 500. In this example, the user has selected the "type-of-visit" option and all of the selectable possibilities for the option are displayed in the pop-up window. The options for pop-up windows or other user interface elements can be customized by the user. Additionally, the patient profile can also be annotated with an indicator designating a member of the medical team who provided input relating to the patient along with any changes to the patient profile resulting from the received input. For example, numeral 501 shows a surgical opinion provided by Dr. Roberto Rodriguez 502 and the date 502 corresponding to the surgical opinion.

This annotation can be performed automatically in response to any changes or updates to the patient profile.

Figure 5B:
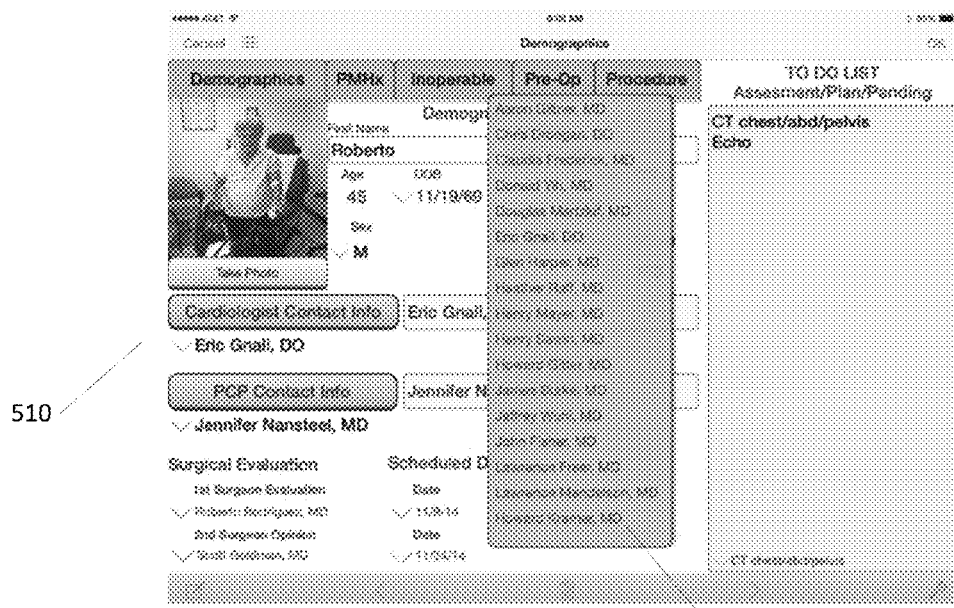

FIG. 5B illustrates another interface 510 of the authenticated API according to an exemplary embodiment. As shown in FIG. 5B, pop-up window 511 listing multiple possible doctors appears in response to the user selecting a data field which requires entry of a doctor, such as cardiologist contact info or PCP contact info. The physicians listed in the pop-up window can be populated from prior records or entries or otherwise be retrieved from either the patient's record or a medical database which keeps track of all doctors and doctor profiles.

Figure 6:
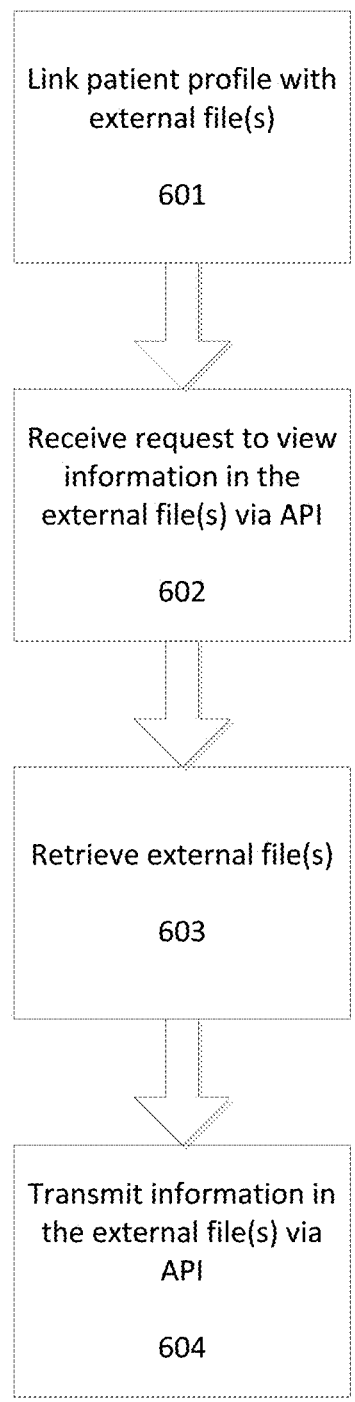
FIG. 6 illustrates a flowchart for retrieving information in an external file through an authenticated API according to an exemplary embodiment.

FIG. 6 is flowchart showing a method of retrieving information in an external file through the authenticated API according to an exemplary embodiment. At step 601 the patient profile is linked with the external file. For example, the patient profile can be linked with one or more external files corresponding to diagnostic test results for the patient. The external files can be stored in, for example, a separate database accessible through the hospital network or through the internet. The linking can be performed by, for example, selecting the file from a drop-down list, pop-up window, or other user interface element which displays files in a linked folder. Alternatively, the user may use the interface to select an external file which is stored locally or remotely accessible. Additionally, the patient profile or multiple patient profiles can be linked to one or more external databases which store files that are of interest to the medical team members.

At step 602 a request to view the information in the external file is received via the authenticated API. This request can be received using a variety of means, such as an interface button, through a drop-down list, or other interface element, or through an automated message (such as an e-mail) sent through the authenticated API. At step 603 the external file is retrieved and at step 604 the requested information in the external files is transmitted via the authenticated API.

Figure 7A:
FIGS. 7A-7D illustrate interfaces for accessing procedure information and viewing follow-up data according to an exemplary embodiment.
Figure 7B:
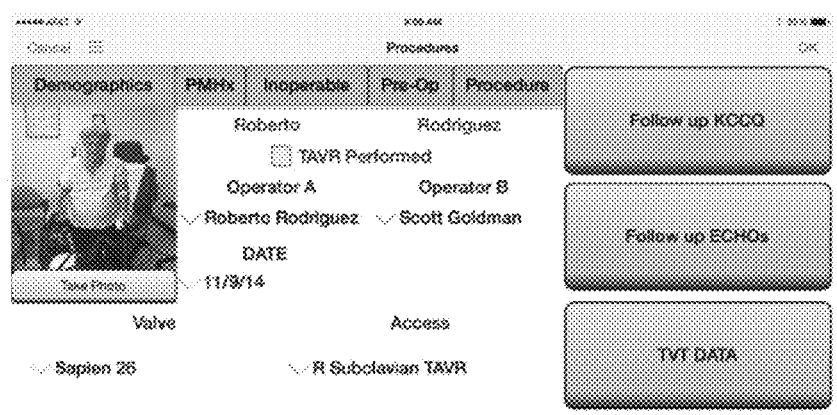
Figure 7C:
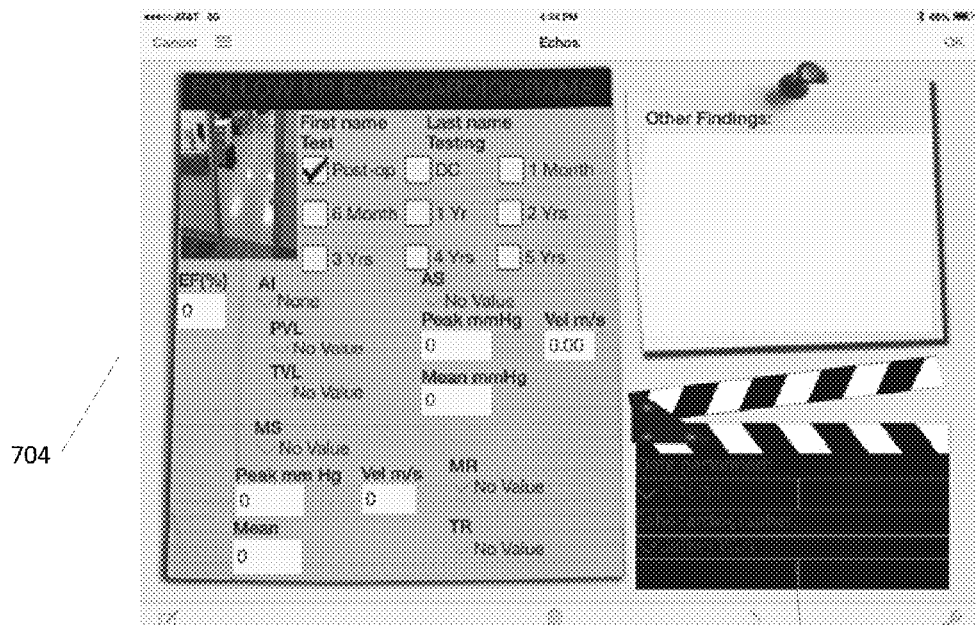

For example, FIG. 7A illustrates an interface 701 of the authenticated API where the medical team has performed a Trans-Apical TAVR procedure 703. Interface 701 can include all the details pertaining to the procedure performed. It can include the name of the main operators selected from a popup menu which is fully customizable. It can contain the type of procedure performed, selected from an editable popup menu and the date the procedure was performed. Interface 701 can include the type of devices implanted/utilized in the procedure, selected from an editable popup menu. Interface 701 can also contain a link to the follow up data, referring physician procedure letters, and the billing data. Additionally, if a user desires to examine follow-up echocardiograms, they can select button 702 to display them through the authenticated API, as shown in FIG. 7C FIG. 7B illustrates another interface 710 of the authenticated API where the medical team has performed a Trans-Apical TAVR procedure. Interface 710 displays much of the same information and options as interface 701 but in a different format. Either interface or some combination of the two can be utilized to display procedure information.

Figure 7D:
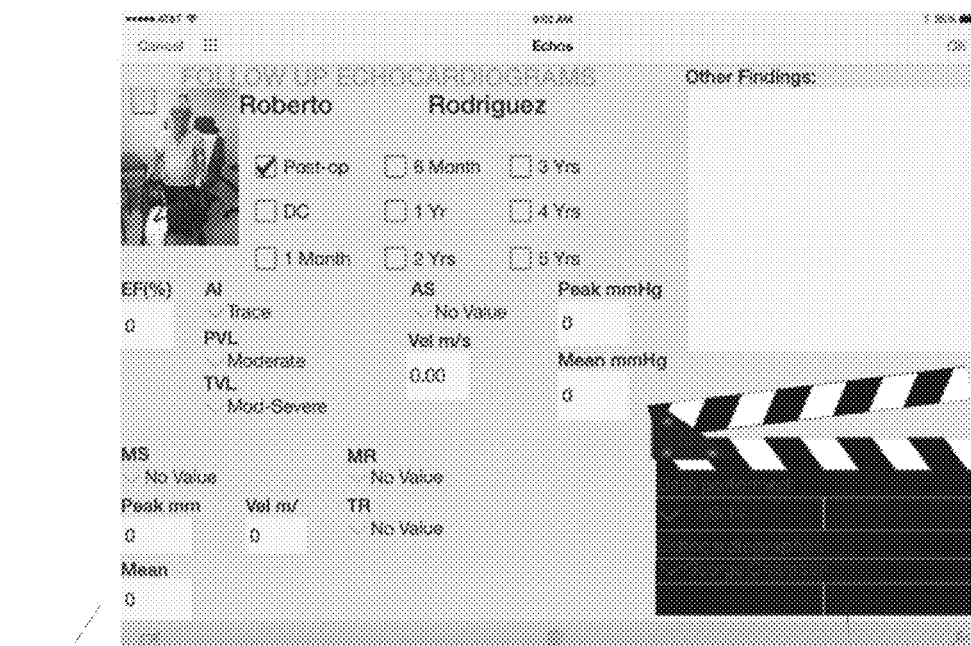

Interfaces 704 and 714 of FIGS. 7C and 7D, respectively, show different possible interfaces corresponding to the follow up echocardiogram information, along with the relevant annotations 705 and 715, such as the date they were performed and the name of the Echocardiographer. Interfaces 704 and 714 also allow the user to enter new information, if desired. The user can then return to the patient profile by pressing a button (such as the cancel button) on the interfaces 704 and 714.

Using the present system, a medical team member can enter a variety of information relating to the patient which will be reflected in the patent profile accessible to all the medical team members (assuming they all have permissions to access the relevant information).

Figure 8:
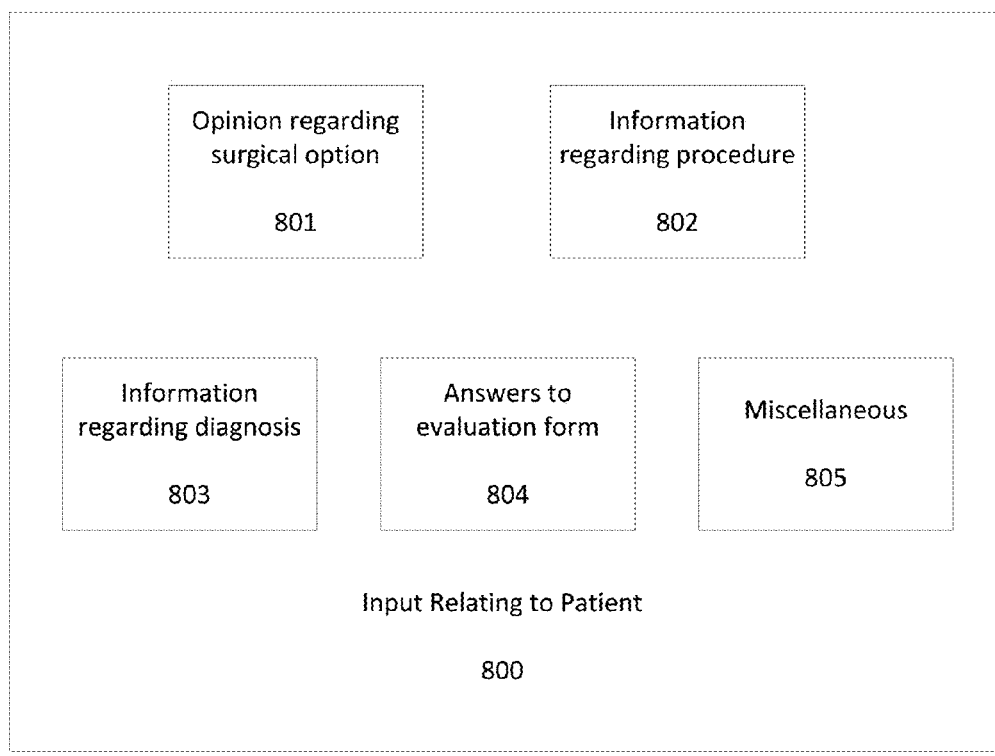
FIG. 8 illustrates multiple types of input relating to a patient according to an exemplary embodiment.

FIG. 8 illustrates the types of input relating to the patient 800 that can be entered through the authenticated API. A medical team member can enter an opinion regarding a surgical option 801 and information regarding a procedure performed on the patient 802. For example, as shown in FIG. 7, a team member has entered information regarding a TAVR performed on the patient 703. A team member can also enter information regarding a diagnosis of the patient 803, answers to an evaluation form about the patient 804, and any miscellaneous information about the patient 805. This can include notes, suggestions, warnings, or any other relevant information about the patient before, during, and after any type of medical intervention.

Figure 9A:
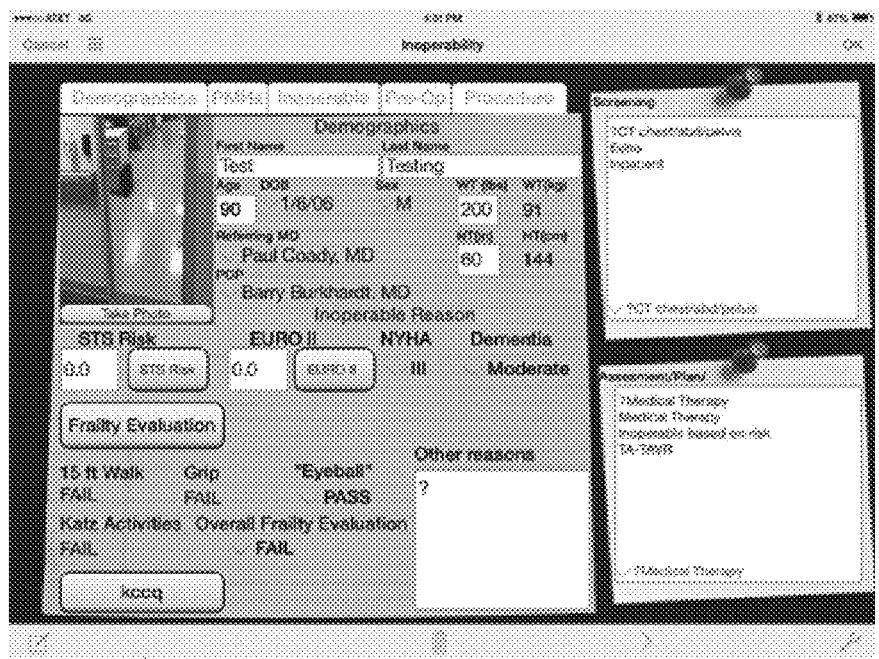

FIG. 9A illustrates an interface 900 of the authenticated API corresponding to the "inoperable" tab in which a user can select a patient evaluation form to complete. The selected patient evaluation form can be integrated into the authenticated API or can be retrieved from an external file and presented in the authenticated API, as discussed earlier. Alternatively, the selected patient evaluation form can be part of a web page which the user is directed to or which is retrieved and then presented within the interface of the authenticated API.

The patient evaluation forms can include a frailty test, a Kansas City Cardiomyopathy Questionnaire (KCCQ), a Society of Thoracic Surgeons (STS) risk evaluation, a European System for Cardiac Operative Risk Evaluation (ESCORE), or any other relevant patient evaluation form or test.

In addition to risk evaluation, the inoperable tab can be used to record other reasons why a particular patient is non-operable or high risk. Identification of alternate reasons for patient eligibility can be documented using pop-up menus in the interface. For TAVR, these include hostile chest, dementia, porcelain aorta, "eyeball test," pulmonary disease, and frailty.

Figure 9B:
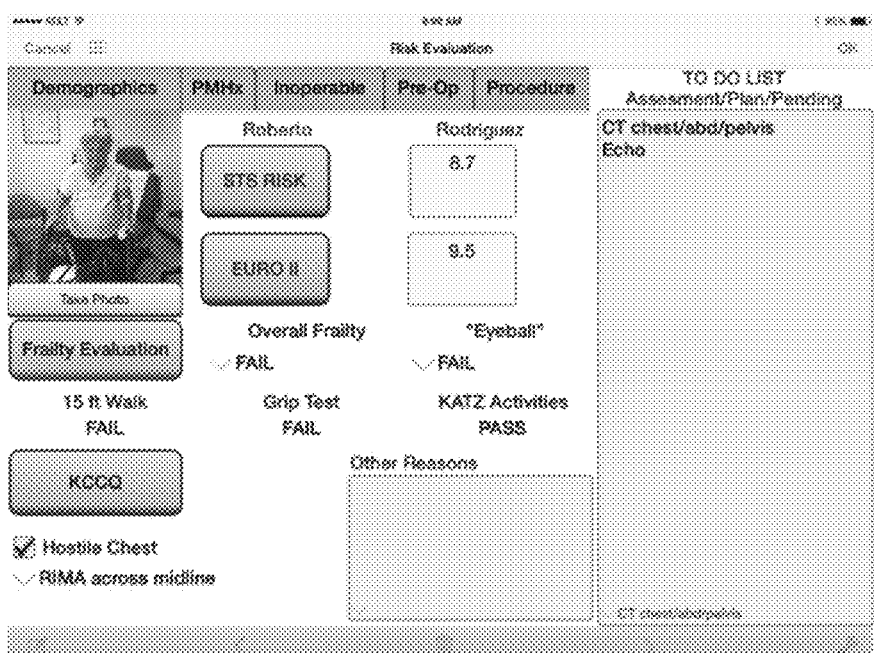

FIG. 9B illustrates another interface 910 of the authenticated API which can also correspond to the "inoperable" tab. As shown in interface 910, the interface 910 can also be labeled "risk evaluation" and can organize the information for various risks and tests in an easily readable format. For example, as shown in interface 910, the patient has failed the frailty, eyeball, 15 ft walk, and grip tests and has passed the Katz activities questionnaire.

Figures 9C, 9D:
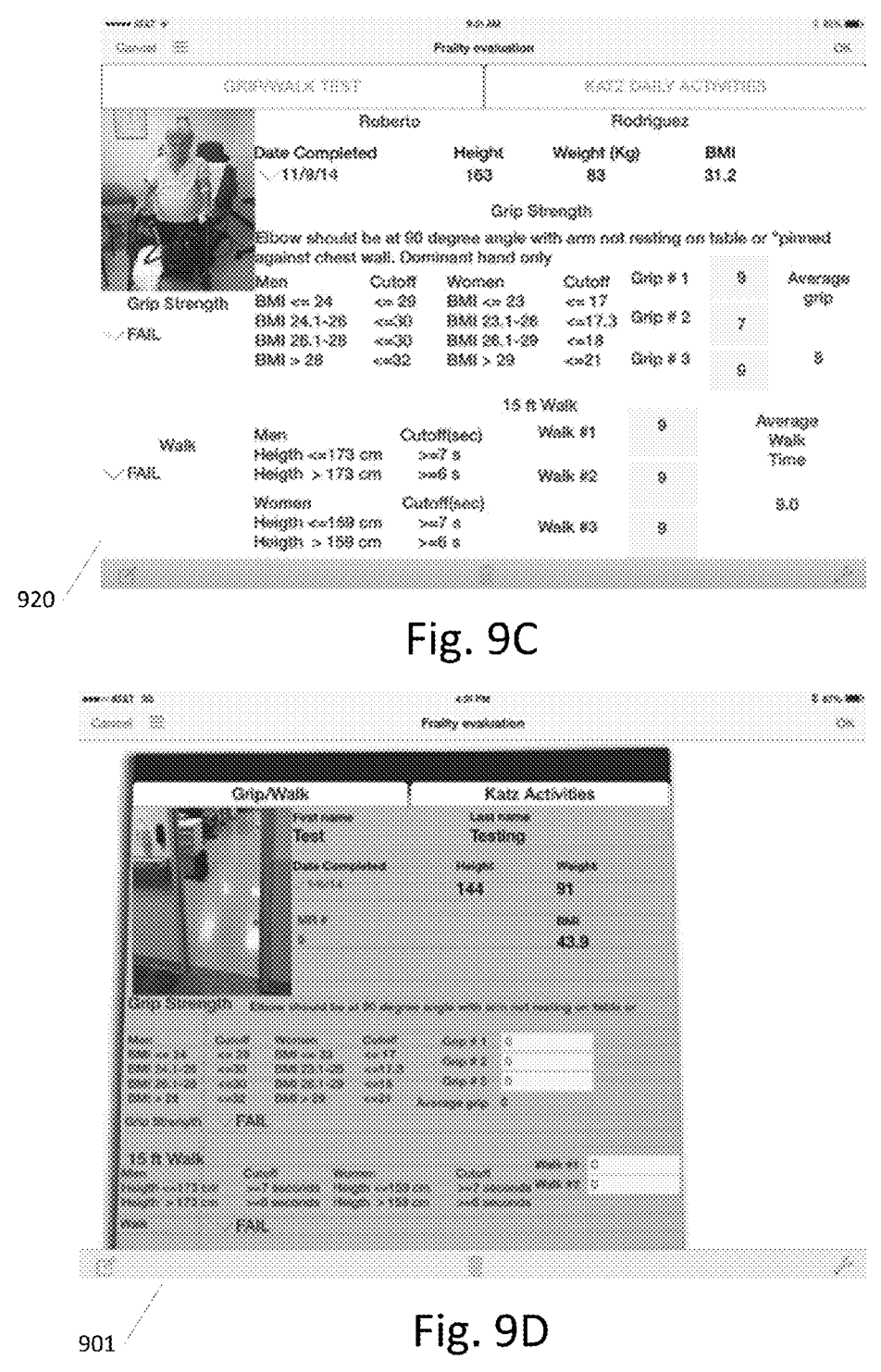
Figure 9E:
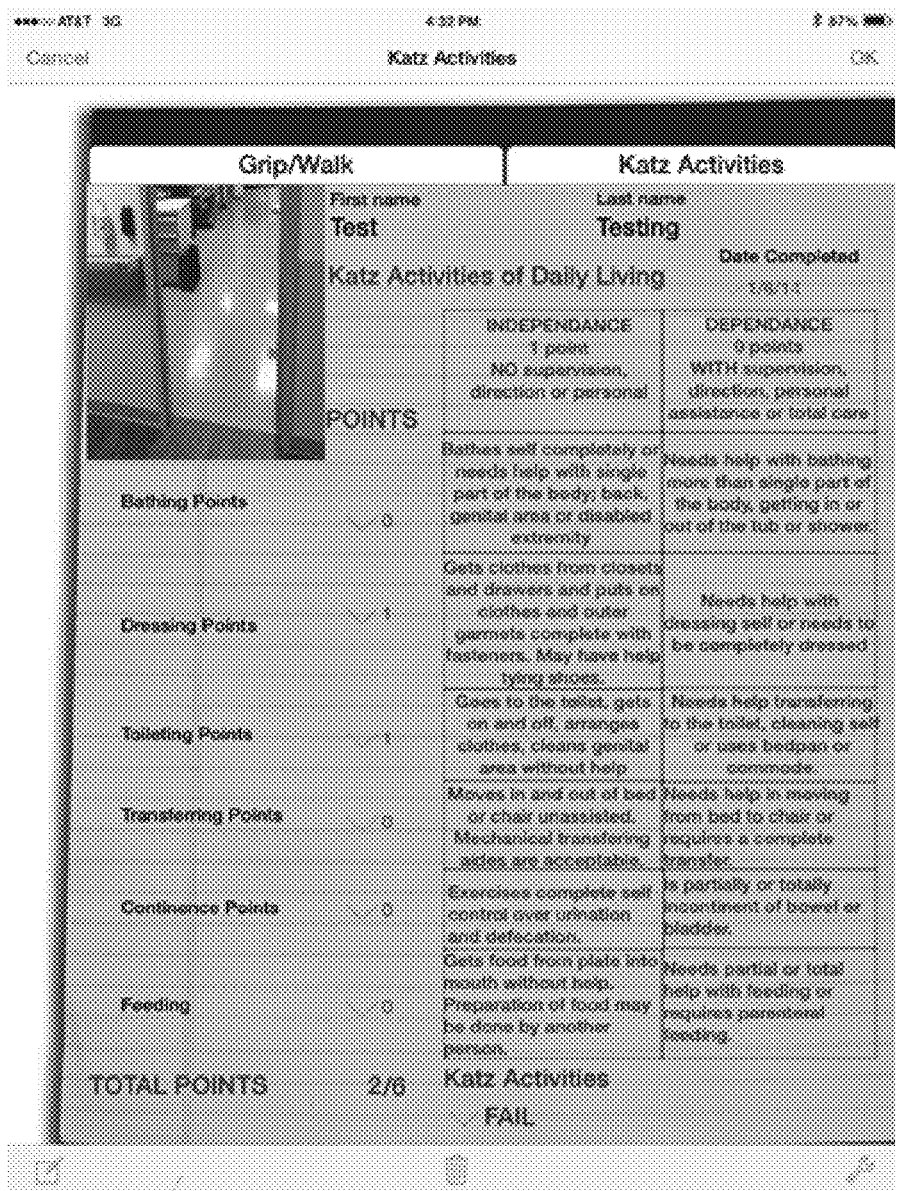
Figure 9F:
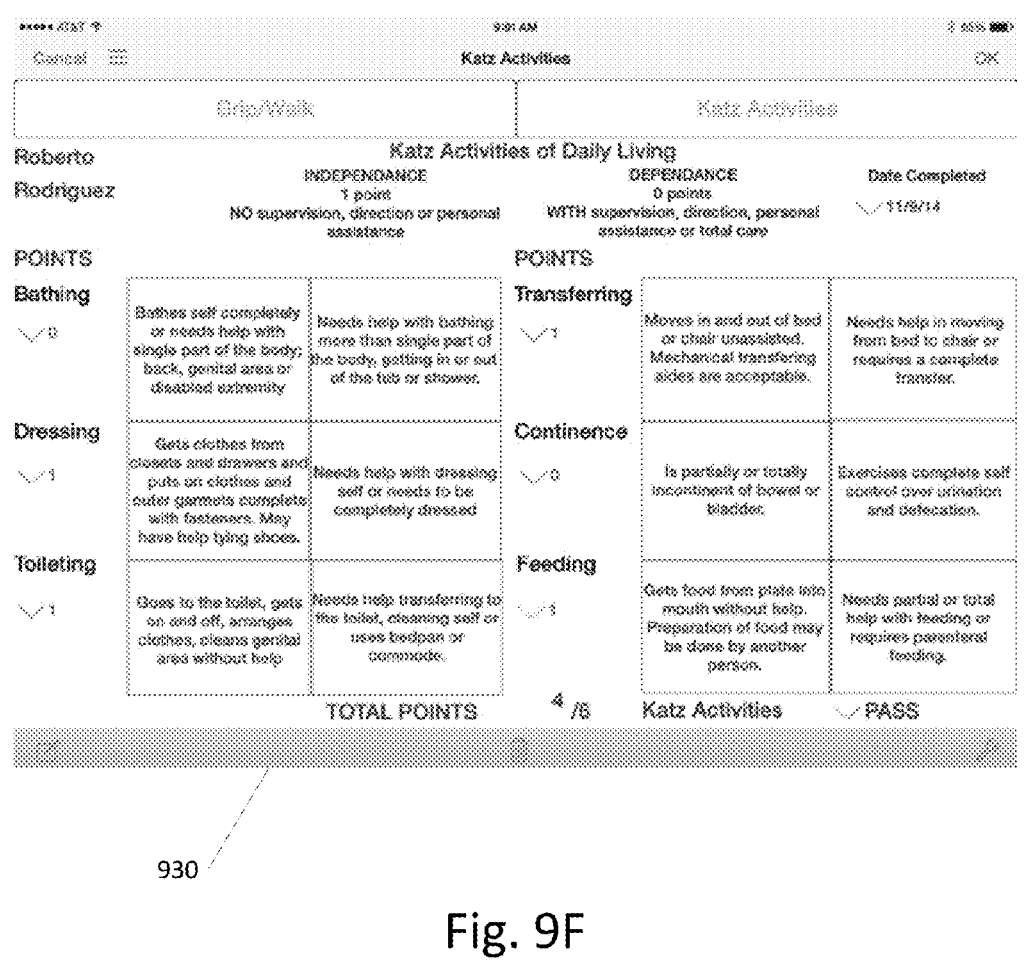
Figure 9G:
Figure 9H:
Figure 9I:
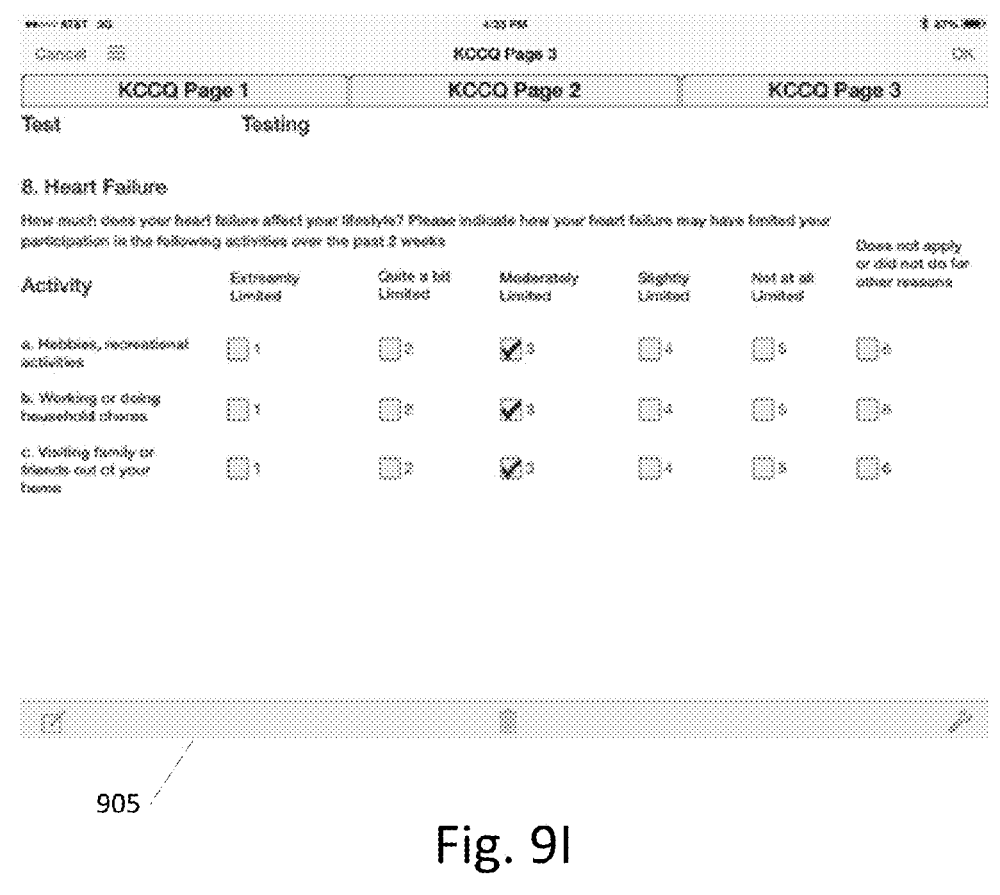

FIGS. 9C-9D illustrate two possible interfaces, 920 and 901, for a grip/walk test which is part of the frailty test. Of course, these interfaces are provided for illustration only can vary according to the particular implementation. FIGS. 9E-9F illustrate two possible interfaces, 902 and 930, for a Katz Activities of Daily Living patient evaluation form which is also part of the frailty test. FIGS. 9G, 9H, and 9I illustrate interfaces 903, 904, and 905, respectively, which are portions of the KCCQ patient evaluation form.

FIG. 10 is a flowchart showing a method for automatically generating a letter pertaining to the patient according to an exemplary embodiment. At step 1001 a request to generate a letter pertaining to the patient is received via the authenticated API. This request can be received by selection of a user interface element. For example, FIG. 4A illustrates an interface 400 containing buttons for a consult letter and a procedure letter. Of course, many types of letters can be automatically generated. For example, the request can be for a referring physician letter, a consultation letter, or a procedure letter.

Figures 10A, 10B:
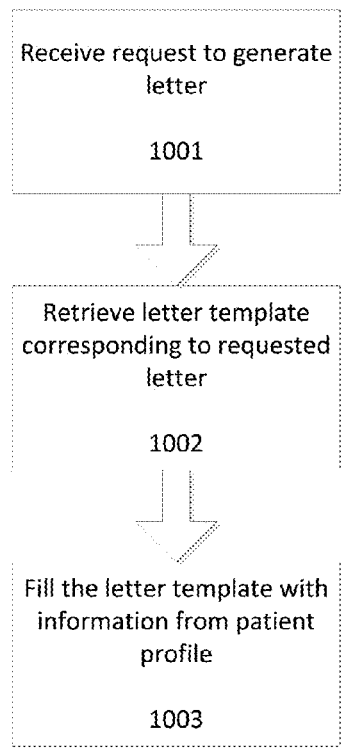
FIG. 10A illustrates a flowchart for generating a letter from a letter template according to an exemplary embodiment.
FIG. 10B illustrates a letter template according to an exemplary embodiment.

At step 1002 a letter template corresponding to the requested letter is retrieved. FIG. 10B illustrates an example letter template 1004. The letter template 1004 can include one or more blank data fields, as shown. Of course, a variety of letter templates can be stored and retrieved based on the type of letter selected. Additionally, users can generate and save their own letter templates. At step 1003 the letter template is filled using information retrieved from the patient profile. For example, the demographic information for the patient can be accessed to retrieve the patient name and the referring physician and the procedure information can be accessed to retrieve the relevant procedure which the letter pertains to. By matching the blank data fields to the corresponding values in the patient profile, the letter can be automatically generated. This saves time and energy for members of the medical team. This letter can then be emailed, faxed, or printed.

In addition to template letters, other types of documents can be generated by a user based on the patient profile. For example, the interface of the API can include buttons to generate procedure notes, consult evaluations, and update documentation that can be printed or delivered via mail, email, or fax.

Figure 11:
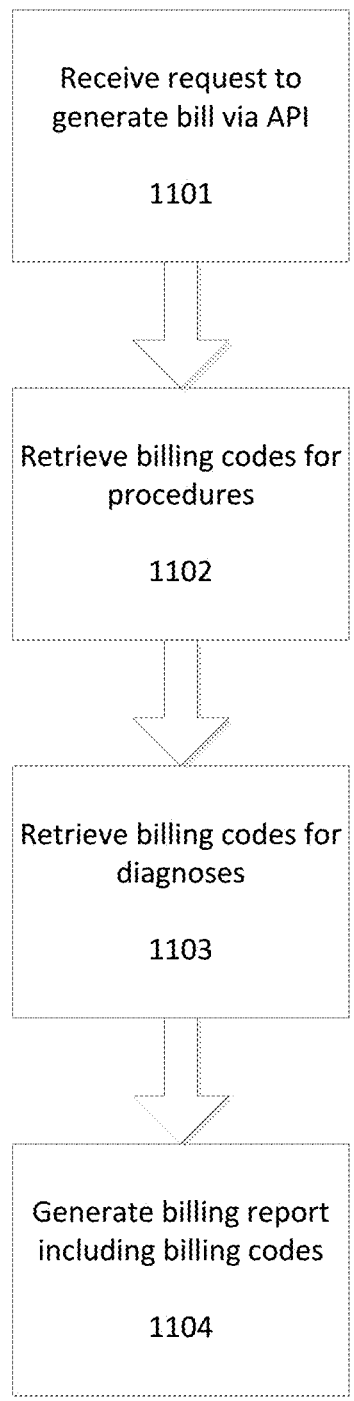
FIG. 11 illustrates a flowchart for generating a billing report according to an exemplary embodiment.

FIG. 11 is a flowchart showing a method for automatically generating a billing report according to an exemplary embodiment. At step 1101 a request to generate a bill is received via the authenticated API. Alternatively, the request can be received outside of the authenticated API, such as by a billing administrator or other professional who does not otherwise have access to the patient profile. At step 1102, one or more billing codes corresponding to one or more procedures associated with the patient profile are retrieved. For example, if the patient had a transcatheter aortic valve placed, a femoral cutdown, aortogram, and a coronary angiogram, then the billing codes for each procedure can be retrieved. More specifically, the one or more procedures associated with the patient profile can be extracted from the patient profile and then cross-referenced with an index of billing codes organized by procedure to retrieve or generate the relevant billing codes. This index can be stored in an external file and then retrieved, as described earlier. Alternatively, the index can be part of the common file or part of the database which hosts the patient profiles.

At step 1103, one or more billing codes corresponding to one or more diagnoses and/or comorbidities associated with the patient profile are retrieved. For example if the patient has hypertension, chronic renal insufficiency and congestive heart failure, the codes for each of these comorbidities can be retrieved. More specifically, the one or more diagnoses associated with the patient profile can be extracted from the patient profile and then cross-referenced with an index of billing codes organized by diagnosis to retrieve or generate the relevant billing codes, similar to the procedure billing codes.

Of course, either step 1102 or step 1103 can be omitted. Alternatively, steps 1102 and 1103 can be combined and all of the relevant billing codes can be retrieved in one step. At step 1104, a billing report including the billing codes is generated. This billing report can be exported to a different application, printed out, or transmitted over email or fax to the patient, to an insurance company, or to an institution's billing department.

Figure 12A:
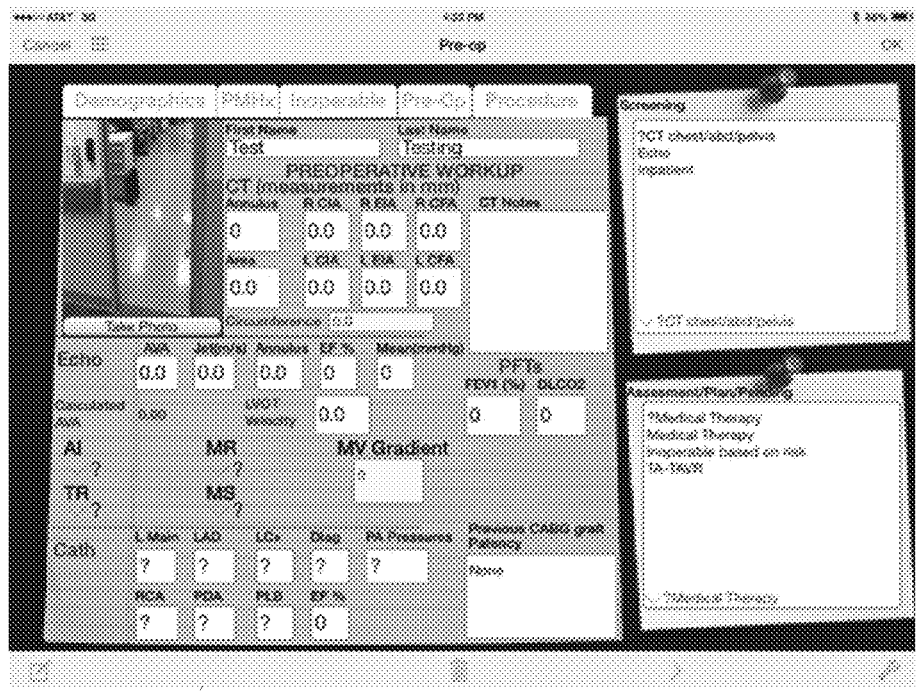
FIGS. 12A-12B illustrate interfaces for accessing and editing patient pre-operative data according to an exemplary embodiment.
Figure 12B:
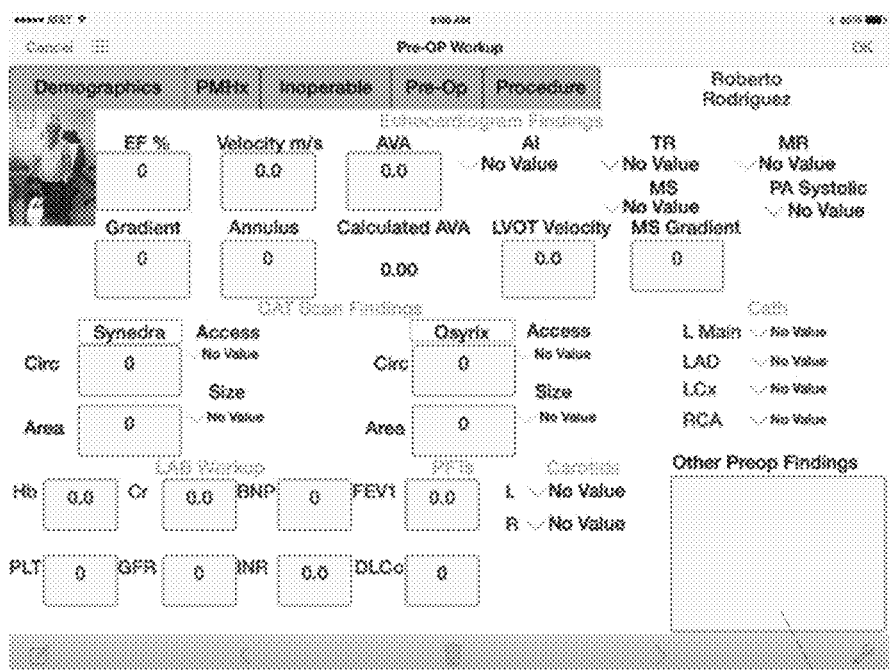

Turning to FIG. 12A, another interface 1200 of the authenticated API is shown according to an exemplary embodiment. Interface 1200 corresponds to the "Pre-Op" tab and allows medical team members to enter information and data values that will be required prior to an operation on the patient. This includes all critical measurements, imaging, laboratory values, preoperative clearance, preoperative requirements, etc. For the TAVR patients, it will contain findings for catheterization, echocardiogram, critical measurements on CT scans and laboratory values, pulmonary function test results, etc. The Pre-Op interface can also include indicators corresponding to requirements that must be fulfilled before the operation can be performed. This can include documentation requirements and opinion requirements, such as a requirement that two surgeons must express concurring opinions regarding a specific issue relating to the patient. Of course, the Pre-Op interface can take many other forms than the one shown in FIG. 12A. For example, FIG. 12B illustrates another interface 1210 of the authenticated API which can correspond to the "Pre-Op" tab. As shown in FIG. 12B, the interface 1210 can include much of the same information as that shown in interface 1200, as well additional options, such as a text entry box 1211 for other Pre-Op findings and notes.

The data created, stored, and exchanged by users of the patient tracking system disclosed herein can be formatted to be compliant with the Health Insurance Portability and Accountability Act (HIPPA). Additionally, some or all of the data can be encrypted for additional protection.

Figure 13:
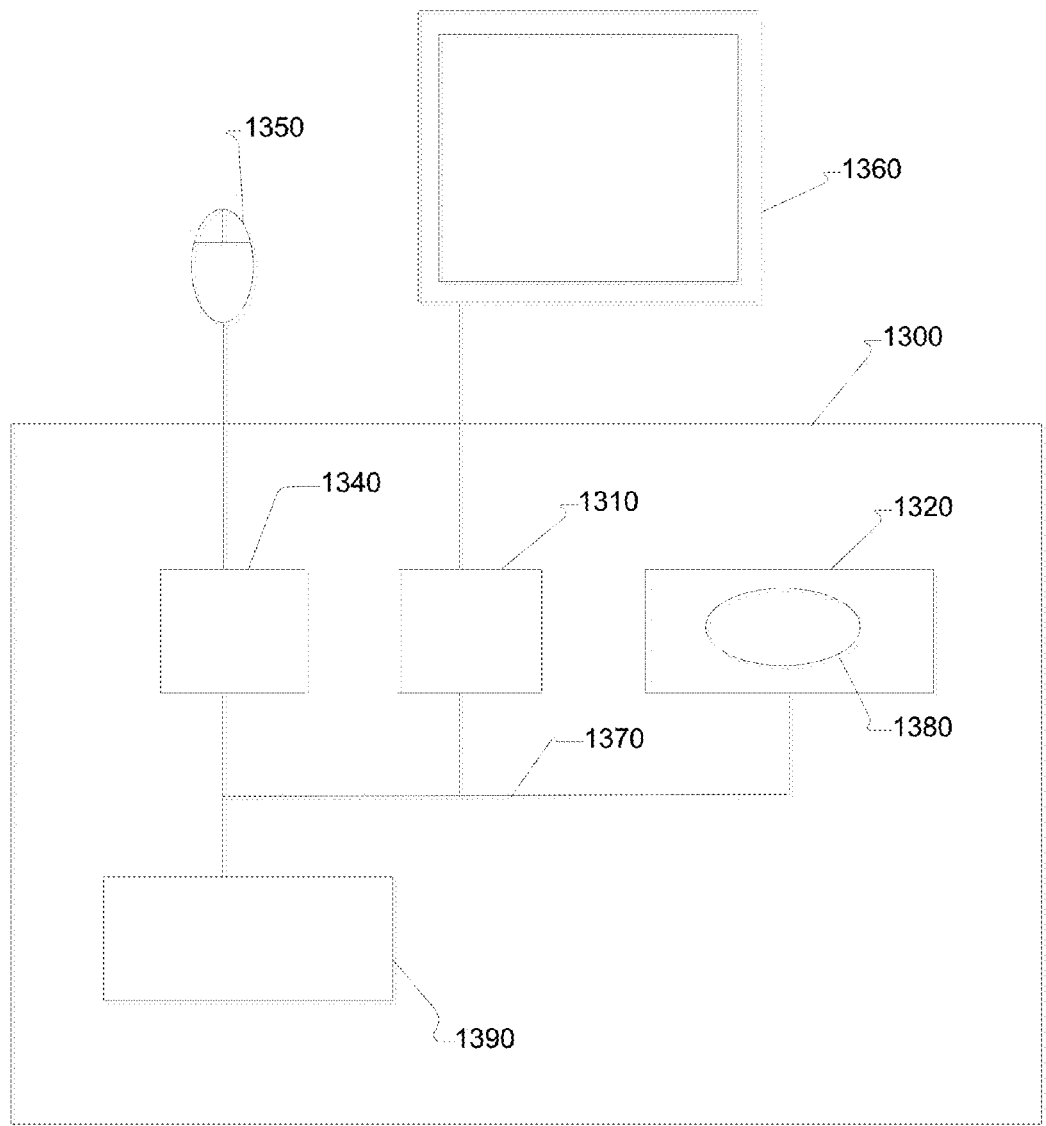
FIG. 13 illustrates an exemplary computing environment that can be used to carry out the method for tracking a patient according to an exemplary embodiment.

One or more of the above-described techniques can be implemented in or involve one or more computer systems. FIG. 13 illustrates a generalized example of a computing environment 1300. The computing environment 1300 is not intended to suggest any limitation as to scope of use or functionality of a described embodiment.

With reference to FIG. 13, the computing environment 1300 includes at least one processing unit 1310 and memory 1320. The processing unit 1310 executes computer-executable instructions and may be a real or a virtual processor. In a multi-processing system, multiple processing units execute computer-executable instructions to increase processing power. The memory 1320 may be volatile memory (e.g., registers, cache, RAM), non-volatile memory (e.g., ROM, EEPROM, flash memory, etc.), or some combination of the two. The memory 1320 may store software instructions 1380 for implementing the described techniques when executed by one or more processors. Memory 1320 can be one memory device or multiple memory devices.

A computing environment may have additional features. For example, the computing environment 1300 includes storage 1340, one or more input devices 1350, one or more output devices 1360, and one or more communication connections 1390. An interconnection mechanism 1370, such as a bus, controller, or network interconnects the components of the computing environment 1300. Typically, operating system software or firmware (not shown) provides an operating environment for other software executing in the computing environment 1300, and coordinates activities of the components of the computing environment 1300.

The storage 1340 may be removable or non-removable, and includes magnetic disks, magnetic tapes or cassettes, CD-ROMs, CD-RWs, DVDs, or any other medium which can be used to store information and which can be accessed within the computing environment 1300. The storage 1340 may store instructions for the software 1380.

The input device(s) 1350 may be a touch input device such as a keyboard, mouse, pen, trackball, touch screen, or game controller, a voice input device, a scanning device, a digital camera, remote control, or another device that provides input to the computing environment 1300. The output device(s) 1360 may be a display, television, monitor, printer, speaker, or another device that provides output from the computing environment 1300.

The communication connection(s) 1390 enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Implementations can be described in the general context of non-transitory computer-readable media. Computer-readable media are any available media that can be accessed within a computing environment. By way of example, and not limitation, within the computing environment 1300, computer-readable media include memory 1320, storage 1340, communication media, and combinations of any of the above.

Of course, FIG. 13 illustrates computing environment 1300, display device 1360, and input device 1350 as separate devices for ease of identification only. Computing environment 1300, display device 1360, and input device 1350 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). Computing environment 1300 may be a set-top box, mobile device, personal computer, or one or more servers, for example a farm of networked servers, a clustered server environment, or a cloud network of computing devices. Mobile devices can include, for example, mobile phones, tablets, laptops, PDAs and/or electronic organizers.

Having described and illustrated the principles of our invention with reference to the described embodiment, it will be recognized that the described embodiment can be modified in arrangement and detail without departing from such principles. It should be understood that the programs, processes, or methods described herein are not related or limited to any particular type of computing environment, unless indicated otherwise. Various types of general purpose or specialized computing environments may be used with or perform operations in accordance with the teachings described herein. Elements of the described embodiment shown in software may be implemented in hardware and vice versa.

In view of the many possible embodiments to which the principles of our invention may be applied, we claim as our invention all such embodiments as may come within the scope and spirit of the following claims and equivalents thereto.

What is claimed is:

1. A method executed by one or more computing devices for integrating and sharing patient-related information among members of a medical team in real-time via an authenticated Application Programming Interface (API), the method comprising:

receiving, by at least one of the one or more computing devices, preliminary patient data corresponding to the patient from a first member of a medical team comprising a plurality of members, wherein the preliminary patient data is received via the authenticated API from a first device;

generating, by at least one of the one or more computing devices, a patient profile for the patient, wherein the patient profile is accessible to each member of the medical team via the authenticated API and wherein the authenticated API is configured to detect any changes to the patient profile;

receiving, by at least one of the one or more computing devices, input relating to the patient from a second member of the medical team, wherein the input is received via the authenticated API from a second device; and updating, by at least one of the one or more computing devices, the patient profile based at least in part on the received input, wherein the updated patient profile is accessible to each of the plurality of members of the medical team via the authenticated API and wherein the authenticated API is configured to:

receive a request to access data from one or more files external to the patient profile which are linked to the patient profile;

retrieve the data from the one or more files external to the patient profile; and output at least a portion of the retrieved data.

2. The method of claim 1, wherein the authenticated API is a password-protected application running on a mobile device.

3. The method of claim 1, wherein the preliminary patient data includes patient medical history.

4. The method of claim 1, wherein the preliminary patient data includes at least one physician associated with the patient.

5. The method of claim 4, wherein the at least one physician associated with the patient comprises at least one of a referring physician and a primary care physician.

6. The method of claim 1, wherein the one or more files external to the patient profile include one or more physician profiles, wherein the request to access data from one or more files external to the patient profile comprises a request to view contact information for a physician associated with the patient and wherein the retrieved data comprises the contact information for the physician associated with the patient.

7. The method of claim 1, further comprising:

annotating, by at least one of the one or more computing devices, the updated patient profile with an indicator designating the second member of the medical team along with the changes in the patient profile resulting from the received input.

8. The method of claim 1, wherein the one or more files external to the patient profile include a plurality of diagnostic test results and wherein the retrieved data comprises one or more diagnostic test results corresponding to the patient.

9. The method of claim 1, wherein the input relating to the patient comprises a recommendation regarding a surgical option.

10. The method of claim 1, wherein the input relating to the patient comprises information regarding a procedure performed on the patient or a diagnosis of the patient.

11. The method of claim 1, wherein the input relating to the patient comprises answers to a patient evaluation form.

12. The method of claim 11, wherein the patient evaluation form is integrated into the authenticated API.

13. The method of claim 11, wherein the patient evaluation form comprises at least one of a frailty test, a Kansas City Cardiomyopathy Questionnaire, a Society of Thoracic Surgeons risk evaluation, and a European System for Cardiac Operative Risk Evaluation.

14. The method of claim 1, wherein the request to access data from one or more files external to the patient profile comprises a request to generate a letter pertaining to the patient, wherein the retrieved data comprises a letter template corresponding to the requested letter including one or more blank data fields, and wherein outputting at least a portion of the retrieved data comprises outputting the letter template with the one or more blank data fields filled with information retrieved from the patient profile.

15. The method of claim 14, wherein the letter comprises at least one of a referring physician letter, a consultation letter, and a procedure letter.

16. The method of claim 1, wherein the request to access data from one or more files external to the patient profile comprises a request to generate a bill, wherein the retrieved data comprises one or more first billing codes corresponding to one or more procedures associated with the patient profile and one or more second billing codes corresponding to one or more diagnoses associated with the patient profile, and wherein outputting at least a portion of the retrieved data comprises outputting a billing report including the one or more first billing codes and the one or more second billing codes.

17. The method of claim 1, wherein the preliminary patient data and the input relating to the patient comprise information indicating the suitability of the patient for a surgical procedure, wherein at least one member of the medical team specializes in the surgical procedure, and wherein the authenticated API tracks one or more requirements that must be fulfilled prior to performing the surgical procedure.

18. An apparatus for integrating and sharing patient-related information among members of a medical team in real-time via an authenticated Application Programming Interface (API), the apparatus comprising:
one or more processors; and
one or more memories operatively coupled to at least one of the one or more processors and having instructions stored thereon that, when executed by at least one of the one or more processors, cause at least one of the one or more processors to:
receive preliminary patient data corresponding to the patient from a first member of a medical team comprising a plurality of members, wherein the preliminary patient data is received via the authenticated API from a first device;
generate a patient profile for the patient, wherein the patient profile is accessible to each member of the medical team via the authenticated API and wherein the authenticated API is configured to detect any changes to the patient profile;
receive input relating to the patient from a second member of the medical team, wherein the input is received via the authenticated API from a second device; and
update the patient profile based at least in part on the received input, wherein the updated patient profile is accessible to each of the plurality of members of the medical team via the authenticated API and wherein the authenticated API is configured to:
receive a request to access data from one or more files external to the patient profile which are linked to the patient profile;
retrieve the data from the one or more files external to the patient profile; and
output at least a portion of the retrieved data.

19. The apparatus of claim 18, wherein the one or more files external to the patient profile include one or more physician profiles, wherein the request to access data from one or more files external to the patient profile comprises a request to view contact information for a physician associated with the patient and wherein the retrieved data comprises the contact information for the physician associated with the patient.

20. The apparatus of claim 18, wherein the one or more files external to the patient profile include a plurality of diagnostic test results and wherein the retrieved data comprises one or more diagnostic test results corresponding to the patient.

21. The apparatus of claim 18, wherein the request to access data from one or more files external to the patient profile comprises a request to generate a letter pertaining to the patient, wherein the retrieved data comprises a letter template corresponding to the requested letter including one or more blank data fields, and wherein outputting at least a portion of the retrieved data comprises outputting the letter template with the one or more blank data fields filled with information retrieved from the patient profile.

22. The apparatus of claim 18, wherein the request to access data from one or more files external to the patient profile comprises a request to generate a bill, wherein the retrieved data comprises one or more first billing codes corresponding to one or more procedures associated with the patient profile and one or more second billing codes corresponding to one or more diagnoses associated with the patient profile, and wherein outputting at least a portion of the retrieved data comprises outputting a billing report including the one or more first billing codes and the one or more second billing codes.

23. At least one non-transitory computer-readable medium storing computer-readable instructions that, when executed by one or more computing devices, cause at least one of the one or more computing devices to:
receive preliminary patient data corresponding to the patient from a first member of a medical team comprising a plurality of members, wherein the preliminary patient data is received via the authenticated API from a first device;
generate a patient profile for the patient, wherein the patient profile is accessible to each member of the medical team via the authenticated API and wherein the authenticated API is configured to detect any changes to the patient profile;
receive input relating to the patient from a second member of the medical team, wherein the input is received via the authenticated API from a second device; and
update the patient profile based at least in part on the received input, wherein the updated patient profile is accessible to each of the plurality of members of the medical team via the authenticated API and wherein the authenticated API is configured to:
receive a request to access data from one or more files external to the patient profile which are linked to the patient profile;
retrieve the data from the one or more files external to the patient profile; and
output at least a portion of the retrieved data.

24. The at least one non-transitory computer-readable medium of claim 23, wherein the one or more files external to the patient profile include one or more physician profiles, wherein the request to access data from one or more files external to the patient profile comprises a request to view contact information for a physician associated with the patient and wherein the retrieved data comprises the contact information for the physician associated with the patient.

25. The at least one non-transitory computer-readable medium of claim 23, wherein the one or more files external to the patient profile include a plurality of diagnostic test results and wherein the retrieved data comprises one or more diagnostic test results corresponding to the patient.

26. The at least one non-transitory computer-readable medium of claim 23, wherein the request to access data from one or more files external to the patient profile comprises a request to generate a letter pertaining to the patient, wherein the retrieved data comprises a letter template corresponding to the requested letter including one or more blank data fields, and wherein outputting at least a portion of the retrieved data comprises outputting the letter template with the one or more blank data fields filled with information retrieved from the patient profile.

27. The at least one non-transitory computer-readable medium of claim 23, wherein the request to access data from one or more files external to the patient profile comprises a request to generate a bill, wherein the retrieved data comprises one or more first billing codes corresponding to one or more procedures associated with the patient profile and one or more second billing codes corresponding to one or more diagnoses associated with the patient profile, and wherein outputting at least a portion of the retrieved data comprises outputting a billing report including the one or more first billing codes and the one or more second billing codes.

* * * * *